(12) United States Patent
Whitton et al.

(10) Patent No.: US 8,124,761 B2
(45) Date of Patent: Feb. 28, 2012

(54) PROCESSES FOR THE PREPARATION OF AZOXYSTROBIN USING DABCO AS A CATALYST AND NOVEL INTERMEDIATES USED IN THE PROCESSES

(75) Inventors: Alan John Whitton, Grangemouth (GB); Ewan Campbell Boyd, Grangemouth (GB); Jack Vass, Grangemouth (GB)

(73) Assignee: Syngenta Limited, Guildford, Surrey (GB)

( * ) Notice: Subject to any disclaimer, the term of this patent is extended or adjusted under 35 U.S.C. 154(b) by 1098 days.

(21) Appl. No.: 11/912,675

(22) PCT Filed: Apr. 13, 2006

(86) PCT No.: PCT/GB2006/001361
§ 371 (c)(1), (2), (4) Date: Oct. 26, 2007

(87) PCT Pub. No.: WO2006/114572
PCT Pub. Date: Nov. 2, 2006

(65) Prior Publication Data
US 2008/0214587 A1    Sep. 4, 2008

(30) Foreign Application Priority Data
Apr. 26, 2005    (GB) .................................. 0508422.3

(51) Int. Cl.
    *C07D 239/52* (2006.01)
(52) U.S. Cl. ...................................................... 544/319
(58) Field of Classification Search .................... 544/319
    See application file for complete search history.

(56) References Cited

U.S. PATENT DOCUMENTS

| | | |
|---|---|---|
| 5,057,146 A | 10/1991 | Anthony et al. |
| 6,153,750 A | 11/2000 | Whitton et al. |
| 6,162,916 A | 12/2000 | Whitton et al. |
| 2003/0092723 A1 | 5/2003 | Weintritt et al. |

FOREIGN PATENT DOCUMENTS

| | | |
|---|---|---|
| EP | 0242081 A1 | 10/1987 |
| GB | 2255092 A | 10/1992 |
| GB | 2291874 A | 2/1996 |
| WO | 92/08703 A | 5/1992 |
| WO | 98/07707 A | 2/1998 |
| WO | 98/18767 A | 5/1998 |
| WO | 01/72719 A | 10/2001 |

*Primary Examiner* — Deepak Rao
(74) *Attorney, Agent, or Firm* — R. Kody Jones

(57) ABSTRACT

The present invention relates, inter alia, to a process for preparing a compound of formula (I): which comprises either (a) reacting a compound of formula (II): with 2-cyanophenyl, or a salt thereof, in the presence of between 0.1 and 2 mol % of 1,4-diazabicyclo[2.2.2]octane, or (b) reacting a compound of the formula (III): with a compound of the formula (IV): in the presence of between 0.1 and 2 mol % of 1,4-diazabicyclo[2.2.2]octane; where W is the methyl (E)-2-(3-methoxy)acrylate group $C(CO_2CH_3)=CHOCH_3$ or the methyl 2-(3,3-dimethoxy)propanoate group $C(CO_2CH_3)CH(OCH_3)_2$, or a mixture of the two groups. In addition, the present invention relates to a novel precursors of the compound of formula (I) and methods for making them.

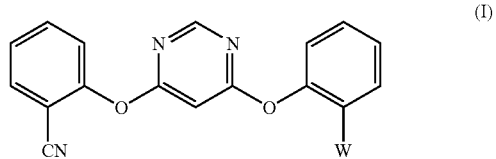

(I)

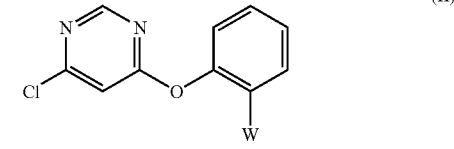

(II)

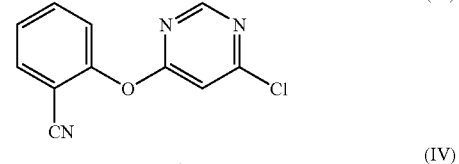

(III)

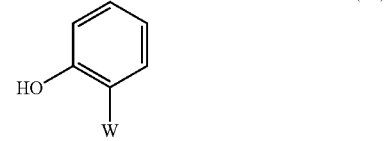

(IV)

12 Claims, No Drawings

PROCESSES FOR THE PREPARATION OF AZOXYSTROBIN USING DABCO AS A CATALYST AND NOVEL INTERMEDIATES USED IN THE PROCESSES

This application is a 371 of International Application No. PCT/GB2006/001361 filed Apr. 13, 2006, which claims priority to GB 0508422.3 filed Apr. 26, 2005, the contents of which are incorporated herein by reference.

The present invention relates to a process for preparing the strobilurin fungicide methyl (E)-2-{2-[6-(2-cyanophenoxy)pyrimidin-4-yloxy]phenyl}-3-methoxyacrylate (azoxystrobin) and a novel precursor thereof.

Methods for preparing azoxystrobin are described in WO 92/08703. In one method, azoxystrobin is prepared by reacting 2-cyanophenyl with methyl (E)-2-[2-(6-chloro-pyrimidin-4-yloxy)phenyl]-3-methoxyacrylate.

A high-yielding method for producing asymmetrical 4,6-bis(aryloxy)pyrimidine derivatives is disclosed in WO 01/72719 in which a 6-chloro-4-aryloxypyrimidine is reacted with a phenol, optionally in the presence of a solvent and/or a base, with the addition of from 2 to 40 mol % of 1,4-diazabicyclo[2.2.2]octane (DABCO).

The present invention is based on the discovery that, when preparing azoxystrobin or a novel acetal precursor of azoxystrobin using DABCO as a catalyst, significantly smaller amounts of this relatively expensive catalyst may be used than are contemplated in WO 01/72719 without compromising the yield. Apart from reducing the cost of manufacture, this has the added environmental benefit of reducing the quantity of catalyst discharged in the aqueous process effluent.

Thus, according to the present invention, there is provided a process for preparing a compound of formula (I):

(I)

wherein W is the methyl (E)-2-(3-methoxy)acrylate group $C(CO_2CH_3)=CHOCH_3$ or the methyl 2-(3,3-dimethoxy)propanoate group $C(CO_2CH_3)CH(OCH_3)_2$, or a mixture of the two groups, which comprises either (a) reacting a compound of formula (II):

(II)

wherein W has the meaning given above, with 2-cyanophenyl, or a salt thereof (suitably potassium 2-cyanophenoxide) in the presence of between 0.1 and 2 mol % of 1,4-diazabicyclo[2.2.2]octane, or (b) reacting the compound of formula (III):

(III)

with a compound of formula (IV):

(IV)

where W has the meaning given above, in the presence of between 0.1 and 2 mol % of 1,4-diazabicyclo[2.2.2]octane.

In a particular embodiment, the process of invention comprises reacting a compound of formula (II):

(II)

wherein W has the meaning given above, with 2-cyanophenyl, or a salt thereof (suitably potassium 2-cyanophenoxide) in the presence of between 0.1 and 2 mol % of 1,4-diazabicyclo[2.2.2]octane.

The compound of formula (I) where W is the methyl 2-(3,3-dimethoxy)propanoate group $C(CO_2CH_3)CH(OCH_3)_2$ [that is, the compound methyl 2-{2-[6-(2-cyanophenoxy)pyrimidin-4-yloxy]phenyl}-3,3-dimethoxypropanoate (hereinafter referred to as 'azoxystrobin acetal')], is a novel compound and forms part of the present invention. In particular, the invention includes isolated azoxystrobin acetal in substantially pure form [that is in an isolated form which comprises from 85 to 100 weight %, preferably from 90 to 100 weight %, of azoxystrobin acetal].

When the process of the invention is carried out using a compound of formula (II) where W is the methyl 2-(3,3-dimethoxy)propanoate group or using a compound of formula (IV) where W is the methyl 2-(3,3-dimethoxy)propanoate group, the product obtained may include a proportion of the compound of formula (I) where W is the methyl (E)-2-(3-methoxy)acrylate group. This may happen because it is possible that methanol is eliminated from the methyl 2-(3,3-dimethoxy)propanoate group under the conditions of the process. For the same reason, if the process is carried out using a compound of formula (II) or a compound of formula (IV) where W is a mixture of the methyl 2-(3,3-dimethoxy)propanoate group and the methyl (E)-2-(3-methoxy)acrylate group (and the invention includes such a process), the product obtained will be a compound of formula (I) where W is a mixture of the methyl 2-(3,3-dimethoxy)propanoate group and the methyl (E)-2-(3-methoxy)acrylate group; however, the product may have a higher proportion of the compound of formula (I) where W is the methyl (E)-2-(3-methoxy)acrylate group than expected from the proportion of (E)-2-(3-methoxy)acrylate group in the mixed starting material due to this potential elimination of methanol. This is of no real consequence because it will normally be required to convert the product of formula (I) where W is the methyl 2-(3,3-dimethoxy)propanoate group to the compound of formula (I) where W is the group methyl (E)-2-(3-methoxy)acrylate group by the elimination of methanol, as discussed later.

Conveniently the process of the invention is carried out in a suitable inert solvent or diluent. These include, for example, aliphatic, alicyclic and aromatic hydrocarbons, such as petroleum ether, hexane, heptane, cyclohexane, methylcyclohexane, benzene, toluene, xylene and decalin; halogenated hydrocarbons, such as chlorobenzene, dichlorobenzene, dichloromethane, chloroform, carbon tetrachloride, dichloroethane and trichloroethane; heteroaromatic solvents such as pyridine or a substituted pyridine, for example, 2,6-dimethylpyridine; ethers, such as diethyl ether, diisopropylether, methyl-tert-butyl ether, methyl-tert-amyl ether, dioxane, tetrahydrofuran, 1,2-dimethoxyethane, 1,2-diethoxyethane and anisole; ketones, such as acetone, butanone, methyl isobutyl ketone and cyclohexanone; nitriles, such as acetonitrile, propionitrile, n- and i-butyronitrile and benzonitrile; amides, such as N,N-dimethylformamide, N,N-dimethylacetamide, N-methylformamide, N-methyl-pyrrolidone and hexamethylphosphoric triamide; tertiary amines, in particular, amines of the formula $R^1R^2R^3N$ where $R^1$, $R^2$ and $R^3$ are each independently $C_{1-10}$ (especially $C_{1-8}$) alkyl, $C_{3-6}$ cycloalkyl, aryl (especially phenyl) or aryl($C_{1-4}$)alkyl (especially benzyl); or two or three of $R^1$, $R^2$ and $R^3$ join together with the nitrogen atom to which they are attached to form one, two or three 5-, 6- or 7-membered alicyclic rings optionally fused and optionally containing a second ring nitrogen atom, examples of suitable tertiary amines being N,N-di-isopropylethylamine (Hünig's base), N,N-dimethylaniline, triethylamine, t-butyldimethyl-amine, N,N-diisopropylmethylamine, N,N-diisopropylisobutylamine, N,N-diisopropyl-2-ethylbutylamine, tri-n-butylamine, N,N-dicyclohexylmethylamine, N,N-dicyclohexylethyl-amine, N-tert-butylcyclohexylamine, N,N-dimethylcyclohexylamine, 1,5-diazabicyclo[4.3.0]-non-5-ene, 1,8-diazabicyclo[5.4.0]undec-7-ene or 2-dimethylaminopyridine; esters, such as methyl acetate, ethyl acetate and isopropyl acetate; sulphoxides, such as dimethylsulphoxide; sulphones, such as sulpholane; and mixtures of such solvents and diluents and mixtures of one or more of them with water. Particularly suitable diluents are ketones [such as methyl isobutyl ketone and cyclohexanone], esters [such as isopropyl acetate], tertiary amines [such as [N,N-diisopropylethylamine (Hünig's base)] and amides [such as N,N-dimethylformamide]. In a particular aspect of the present invention, methyl isobutyl ketone is used as diluent. In a further aspect of the present invention, cyclohexanone is used as diluent. In a further aspect of the present invention, isopropyl acetate is used as diluent. In a further aspect of the present invention, N,N-dimethylformamide is used as diluent. In a further aspect of the present invention, N,N-diisopropylethylamine (Hünig's base) is used as diluent. Most suitably, the diluent used in the present invention is N,N-dimethylformamide.

In a further embodiment of the present invention, the process is carried out in aqueous two phase solvent system. Suitably, in this embodiment, when the compound of formula (II) is reacted with 2-cyanophenyl, the 2-cyanophenyl is present as a salt. Most suitably, the salt is potassium 2-cyanophenoxide. Advantageously, the water is removed throughout the reaction. Suitable co-solvents for use in such an aqueous process are solvents which are at least partially water immiscible solvents such as cyclohexanone, methyl isobutyl ketone and isopropyl acetate. Most suitably, when such an aqueous system is used, the salt of 2-cyanophenyl is potassium 2-cyanophenoxide and the diluent is cyclohexanone, methyl isobutyl ketone or isopropyl acetate. It is noted that when the 2-cyanophenyl is added to the process as an aqueous solution of potassium 2-cyanophenoxide it is possible to reduce the quantity of acid acceptor (see below) used.

In addition, the process of the invention is conveniently carried out in the presence of an acid acceptor. Suitable acid acceptors are all customary inorganic and organic bases. These include, for example, alkaline earth metal and alkali metal hydroxides, acetates, carbonates, bicarbonates and hydrides [such as sodium hydroxide, potassium hydroxide, sodium acetate, potassium acetate, sodium carbonate, potassium carbonate, sodium bicarbonate, potassium bicarbonate, calcium hydride, sodium hydride and potassium hydride], guanidines, phosphazines (see, for example, *Liebigs Ann.* 1996, 1055-1081), prophosphatranes (see, for example, JACS 1990, 9421-9422) and tertiary amines [such as those described above as possible solvents or diluents]. Particularly suitable acid acceptors are the alkaline earth metal and alkali metal carbonates, especially potassium carbonate and sodium carbonate and the tertiary amines 1,5-diazabicyclo[4.3.0] non-5-ene and 1,8-diazabicyclo[5.4.0]undec-7-ene. More suitably, the acid acceptor is potassium carbonate. Most suitably, the present invention is carried out in the presence of methyl isobutyl ketone, cyclohexanone, isopropyl acetate, N,N-diisopropylethylamine (Hünig's base) or N,N-dimethylformamide with potassium carbonate as the acid acceptor.

The process of the invention is carried out in the presence of between 0.1 and 2 mol % of 1,4-diazabicyclo[2.2.2]octane (DABCO), that is more than 0.1 but less than 2 mol % of DABCO. Preferably, it is carried out in the presence of between 0.2 and 2 mol % of DABCO. Any amount of DABCO between 0.1 or 0.2 and 2, 0.1 or 0.2 and 1.9, 0.1 or 0.2 and 1.8, 0.1 or 0.2 and 1.7, 0.1 or 0.2 and 1.6 and 0.1 or 0.2 and 1.5 mol % is suitable, but the invention is of especial benefit in that the amount of DABCO used may be between 0.2 and 1.4 mol %. Normally it will be between 0.5 and 1.4 mol %, typically between 0.8 and 1.2 mol %, for example, about 1 mol %.

In a particular embodiment of the invention the process is carried out in the presence of about 1 mol % DABCO with methyl isobutyl ketone, cyclohexanone, isopropyl acetate, N,N-diisopropylethylamine (Hünig's base), or N,N-dimethylformamide as diluent. Most suitably, the diluent is N,N-dimethylformamide. Suitably, the acid acceptor will be potassium carbonate.

When carrying out the process of the invention, the reaction temperature can be varied within a relatively wide range. The temperature chosen will depend on the nature of the solvent or diluent, for example on its boiling point and/or its effectiveness for promoting the desired reaction, and on the speed at which the reaction is to be carried out. In any given solvent or diluent, the reaction will tend to progress more slowly at lower temperatures. In general, the reaction may be carried out at a temperature of from 0 to 120° C., suitably at a temperature of from 40 to 100° C., and typically at a temperature of from 45 to 95° C., for example, from 60 to 85° C.

For carrying out the process of the invention, from 0.8 to 4 mol, usually from 0.95 to 1.2 mol, of 2-cyanophenyl is employed per mol of a compound of formula (II); and similar amounts (0.8 to 4 mol, usually from 0.95 to 1.2 mol) of a compound of formula (IV) are employed per mole of the compound of formula (III).

Conveniently the process of the invention is carried out by mixing one of the components of the reaction, preferably in the presence of a solvent or diluent, with a base. The other component is then added, if appropriate in the presence of a solvent or diluent, and the mixture is stirred, normally at an elevated temperature. The DABCO catalyst may be added at any stage but is preferably added as the last component, as this tends to promote higher product yields. After the reaction is judged to be complete, the reaction mixture is worked up and the product is isolated using conventional techniques well known to a skilled chemist.

2-Cyanophenol is a commercially available material.

The compound of formula (II), where W is the methyl (E)-2-(3-methoxy)acrylate group $C(CO_2CH_3)=CHOCH_3$, and the compound of formula (II) where W is the methyl 2-(3,3-dimethoxy)propanoate group $C(CO_2CH_3)CH(OCH_3)_2$, may be prepared as described in WO 92/08703 from the reaction of 3-(α-methoxy)methylenebenzofuran-2(3H)-one (derived from benzofuran-2(3H)-one) with 4,6-dichloropyrimidine. The compound of formula (II), where W is the methyl (E)-2-(3-methoxy)acrylate group, may also be prepared by eliminating methanol from (that is, by the demethanolysis of) the compound of formula (II) where W is the methyl 2-(3,3-dimethoxy)propanoate group, as described in WO 92/08703 or WO 98/07707. The compound of formula (II), where W is the methyl 2-(3,3-dimethoxy)propanoate group, may be prepared as described in GB-A-2291874 by reacting a compound of formula (IV), where W is the methyl 2-(3,3-dimethoxy)propanoate group, with 4,6-dichloropyrimidine. It may be purified before use by known techniques or may be used in an unpurified state from a previous reaction, for example, in a 'one-pot' reaction.

The compound of formula (IV), where W is the methyl 2-(3,3-dimethoxy)propanoate group, may be prepared as described in GB-A-2291874 from 3-(α-methoxy)methylenebenzofuran-2(3H)-one. The compound of formula (IV), where W is the methyl (E)-2-(3-methoxy)acrylate group, may be prepared by the demethanolysis of the compound of formula (IV) where W is the methyl 2-(3,3-dimethoxy)propanoate group. In this case the phenolic group needs to be protected by, for example, benzylation before demethanolysis and then de-protected afterwards.

In a further aspect, the present invention includes a process for preparing a compound of formula (IV) where W is the methyl (E)-2-(3-methoxy)acrylate group, which comprises the steps of:

(i) reacting the compound of formula (IV) where W is the methyl 2-(3,3-dimethoxy)-propanoate group with a reagent that will protect the hydroxyl group of that compound from reaction during subsequent demethanolysis;

(ii) eliminating methanol from the hydroxyl-protected compound formed in step (i); and (iii) removing the hydroxyl-protecting group formed in step (i) to form a compound of formula (IV) where W is the methyl (E)-2-(3-methoxy)acrylate group.

In step (i) of the process, the compound of formula (IV) where W is the methyl 2-(3,3-dimethoxy)propanoate group is reacted with a standard protecting reagent, such as a benzyl halide or a substituted benzyl halide [such as a 2-nitrobenzyl halide], for example, benzyl bromide or 2-nitrobenzyl bromide, conveniently in a suitable solvent, such as N,N-dimethylformamide, and a suitable base, such as potassium carbonate, to form a compound of formula (V):

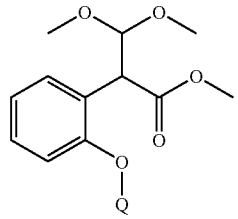

(V)

where Q is a protecting group, such as benzyl or 2-nitrobenzyl.

In step (ii) of the process, methanol is eliminated by any suitable physical or chemical means, for example, as described in WO 92/08703 or WO 98/07707. Conveniently, it is eliminated by treating a compound of formula (V) with methanesulphonic acid in the presence of acetic anhydride at a temperature in the range of, for instance, from 20° C. to 110° C., typically from 20° C. to 80° C. and preferably from 30° C. to 60° C., for example, at about 40° C.

In step (iii) of the process, the protecting group may be removed by any standard technique for removing protecting groups, for example, by a reduction technique using hydrogen with a 10% palladium/carbon catalyst in ethyl acetate at ambient temperature.

The invention also includes novel intermediates of formula (V) where Q is a protecting group, and particularly the intermediate of formula (V) where Q is benzyl [that is, the compound methyl 2-(2-benzyloxy)phenyl-3,3-dimethoxypropanoate]. More particularly, the invention includes isolated methyl 2-(2-benzyloxy)phenyl-3,3-dimethoxypropanoate in substantially pure form [that is, in an isolated form which comprises from 85 to 100 weight %, preferably from 90 to 100 weight %, of methyl 2-(2-benzyloxy)phenyl-3,3-dimethoxy-propanoate].

The following Examples illustrate the invention. Throughout the Examples the following abbreviations are used:
DMF=dimethylformamide   DABCO=1,4-diazabicyclo[2.2.2]octane
MIBK=methyl isobutyl ketone   NMR=nuclear magnetic resonance
MHz=megahertz Ar=aryl Py=pyrimidinyl

EXAMPLES

Example 1

This example describes a sequence of experiments designed to show the effect of decreasing the concentration of DABCO.

a) Coupling of methyl (E)-2-{2-[6-chloropyrimidin-4-yloxy]phenyl}-3-methoxyacrylate with 2-cyanophenyl in DMF with 2 mol % DABCO A slurry containing methyl (E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenyl (33.6 g at 97.5%, 0.275 mols) in DMF (130 mls) was heated to approximately 60° C. A solution of DABCO (0.56 g, 0.005 mols) in DMF (10 mls) was added. The mixture was heated to 80° C. and held at this temperature for 60 minutes. The DMF was removed by vacuum distillation. Toluene (160 ml) and water (265 mls) were added to the distillation residues and the two phase mixture heated to 70-80° C. The mixture was stirred for 40 minutes then settled and the lower aqueous phase separated. The toluene solution (237.8 g) contained methyl (E)-2-{2-[6-(2-cyanophenoxy)pyrimidin-4-yloxy]phenyl}-3-methoxyacrylate (41.3% w/w) 97.5% of theory.

b) Coupling of methyl (E)-2-{2-[6-chloropyrimidin-4-yloxy]phenyl}-3-methoxyacrylate with 2-cyanophenyl in DMF with 1 mol % DABCO.

A slurry containing methyl (E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenyl (33.6 g at 97.5%, 0.275 mols) in DMF (130 mls) was heated to approximately 60° C. A solution of DABCO (0.28 g, 0.0025 mols) in DMF (10 mls) was added. The mixture was heated to 80° C. and held at this temperature for 60 minutes. The DMF was removed by vacuum distillation. Toluene (160 ml) and water (265 mls) were added to the distillation residues and the two phase mixture heated to 70-80° C. The mixture was stirred for 40 minutes then settled and the lower aqueous phase separated. The toluene solution (227.9 g) contained methyl (E)-2-{2-[6-(2-cyanophenoxy)pyrimidin-4-yloxy]phenyl}-3-methoxyacrylate (43.6% w/w) 98.7% of theory.

c) Coupling of methyl (E)-2-{2-[6-chloropyrimidin-4-yloxy]-phenyl}-3-methoxyacrylate with 2-cyanophenyl in DMF with 0.2 mol % DABCO.

A slurry containing methyl (E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenyl (33.6 g at 97.5%, 0.275 mols) in DMF (130 mls) was heated to approximately 60° C. A solution of DABCO (0.056 g, 0.0005 mols) in DMF (10 mls) was added. The mixture was heated to 80° C. and held at this temperature for 300 minutes. The DMF was removed by vacuum distillation. Toluene (160 ml) and water (265 mls) at 60° C. were added to the distillation residues and the two phase mixture heated to 70-80° C. The mixture was stirred for 40 minutes then settled and the lower aqueous phase separated. The toluene solution (243.1 g) contained methyl (E)-2-{2-[6-(2-cyanophenoxy)pyrimidin-4-yloxy]phenyl}-3-methoxyacrylate (38.6% w/w), 93.1% of theory.

d) Coupling of methyl (E)-2-{2-[6-chloropyrimidin-4-yloxy]phenyl}-3-methoxyacrylate with 2-cyanophenyl in DMF with 0.1 mol % DABCO.

A slurry containing methyl (E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenyl (33.6 g at 97.5%, 0.275 mols) in DMF (130 mls) was heated to approximately 60° C. A solution of DABCO (0.028 g, 0.00025 mols) in DMF (10 mls) was added. The mixture was heated to 80° C. and held at this temperature for 300 minutes. The DMF was removed by vacuum distillation. Toluene (160 ml) was added to the distillation residues, maintaining the temperature between 70-80° C., followed by water (265 mls) which had been heated to 60° C. The mixture was stirred for 40 minutes at 80° C. and then settled and the lower aqueous phase separated. The toluene solution (226.7 g) contained methyl (E)-2-{2-[6-(2-cyanophenoxy)pyrimidin-4-yloxy]phenyl}-3-methoxyacrylate (41.5% w/w), 93.4% of theory.

e) Coupling of methyl (E)-2-{2-[6-chloropyrimidin-4-yloxy]phenyl}-3-methoxyacrylate with 2-cyanophenyl in DMF with no DABCO present.

A slurry containing methyl (E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenyl (33.6 g at 97.5%, 0.275 mols) in DMF (130 mls) was heated to approximately 80° C. and held at this temperature for 8 hours. The DMF was removed by vacuum distillation to a maximum temperature of 100° C. Toluene (160 ml) was added to the distillation residues, maintaining the temperature between 60-70° C., followed by water (265 mls) which had been heated to 60° C., again maintaining the temperature between 60-70° C. The mixture was stirred for 40 minutes at 80° C. and then settled and the lower aqueous phase separated. The toluene solution (223.3 g) contained methyl (E)-2-{2-[6-(2-cyanophenoxy)pyrimidin-4-yloxy]phenyl}-3-methoxyacrylate (38.8% w/w) 86.6% of theory.

A summary of the results of these experiments is shown in the following table:

TABLE 1

| Concentration of DABCO | Azoxystrobin recovered (% of theory) |
|---|---|
| 2.0 mol % | 97.5 |
| 1.0 mol % | 98.7 |
| 0.2 mol % | 93.1 |
| 0.1 mol % | 93.4 |
| Zero | 86.6 |

As can be seen, surprisingly, the yield of azoxystrobin formed in the process did not decrease greatly when the DABCO concentration was decreased below 2 mol %: even concentrations of DABCO of as low as 0.1 mol % were sufficient to give a yield of 93.4% of theory. In addition, it is noted that, not only did the experiment containing no DABCO give a much lower yield, it also required 8 hours to reach this point compared to 5 hours for 0.1 mol % and 0.2 mol % DABCO and 60 minutes for 1.0 mol % and 2.0 mol % DABCO (in this respect, it is also noted that the experiment containing 1.0 mol % DABCO surprisingly gave the a similar yield in the same time as the experiment containing 2.0 mol % DABCO).

Example 2

Further individual experiments were carried out to investigate the yield obtained with low levels of DABCO when a variety of solvents were used. In addition, in Example 2c) characterising data for methyl 2-{2-[6-(2-cyanophenoxy)pyrimidin-4-yloxy]phenyl}-3,3-dimethoxypropanoate are given.

a) The preparation of azoxystrobin by the coupling of 2-cyanophenyl and methyl (E)-2-{2-[6-chloropyrimidin-4-yloxy]phenyl}-3-methoxyacrylate in DMF with 1 mol % DABCO.

To a solution of methyl (E)-2-{2-[6-chloropyrimidin-4-yloxy]phenyl}-3-methoxyacrylate (96.2 g; prepared as described in WO 92/08703) in DMF (approximately 100 g) was added a DMF solution of 2-cyanophenyl (78.5 g at 50% w/w 2-cyanophenyl) followed by potassium carbonate (63.5 g) and DABCO (0.34 g). The mixture was heated to 80° C. and held for 75 minutes. The DMF was removed by vacuum distillation to a final temperature of 100° C. Toluene (165.8 g) was charged to the distillation residues and the temperature brought to 75° C. before adding hot water (318.6 g) and stirring for 30 minutes at 80° C. The aqueous phase was removed and then the toluene layer was sampled and analysed. The solution yield of methyl (E)-2-{2-[6-(2-cyanophenoxy)pyrimidin-4-yloxy]phenyl}-3-methoxyacrylate (azoxystrobin) was 90.0%. The toluene was distilled off under vacuum. Methanol (88 g) was added to the distillation residues at 70° C. and the mixture cooled to <5° C., filtered and the cake washed with methanol (2×30 ml) to give, after drying, methyl (E)-2-{2-[6-(2-cyano-phenoxy)pyrimidin-4-yloxy]phenyl}-3-methoxyacrylate (83.2% yield).

b) The preparation of azoxystrobin by the coupling of 2-cyanophenyl and methyl (E)-2-{2-[6-chloropyrimidin-4-yloxy]phenyl}-3-methoxyacrylate in cyclohexanone with 0.9 mol % DABCO.

To a solution of methyl (E)-2-{2-[6-chloropyrimidin-4-yloxy]phenyl}-3-methoxyacrylate (64.4 g; prepared as described in WO 92/08703) in cyclohexanone (approximately 80 g) was added 2-cyanophenyl (26.6 g) and cyclohexanone (26.6 g). The mixture was heated to 50° C. and DABCO (0.2 g) in cyclohexanone (2 g) and potassium carbonate (42.4 g) were charged. The reaction was heated to 90° C. and held for three hours. The temperature was adjusted to 50-60° C. and hot water (88 g) added, stirred for 15 minutes, and the aqueous phase separated. Analysis of the cyclohexanone layer gave a 91.3% yield of methyl (E)-2-{2-[6-(2-cyanophenoxy)pyrimidin-4-yloxy]phenyl}-3-methoxyacrylate (azoxystrobin). Cyclohexanone was removed by vacuum distillation, and to the distillation residues at 80° C. was added methanol (59 g). The methanol solution was cooled slowly to 0-5° C., filtered and the cake washed with methanol (2×15.8 g) to give, after drying, methyl (E)-2-{2-[6-(2-cyanophenoxy)pyrimidin-4-yloxy]phenyl}-3-methoxyacrylate (87.0% yield).

c) The preparation of azoxystrobin and azoxystrobin acetal by the coupling of 2-cyanophenyl and methyl 2-{2-[6-chloropyrimidin-4-yloxy]phenyl}-3,3-dimethoxypropanoate in cyclohexanone with 1.0 mol % DABCO.

A crude mixture (53 g) containing methyl 2-{2-[6-chloropyrimidin-4-yloxy]phenyl}-3,3-dimethoxypropanoate (43 g) and methyl (E)-2-{2-[6-chloropyrimidin-4-yloxy]phenyl}-3-methoxyacrylate (6.1 g) (prepared as described in WO 92/08703) was dissolved in cyclohexanone (156 g). Potassium carbonate (21.9 g), 2-cyanophenyl (15.6 g) and DABCO (0.14 g) were added and the mixture heated to 90° C. and held at this temperature for 4 hours. Water (100 ml) was added at 90° C. and the mixture stirred for 10 minutes, settled and the aqueous phase separated. Aqueous hydrochloric acid (1%) and sodium chloride (10 g) were added and the mixture stirred, settled and the water layer removed. Analysis of the cyclohexanone solution revealed methyl 2-{2-[6-(2-cyanophenoxy)pyrimidin-4-yloxy]phenyl}-3,3-dimethoxypropanoate (73%) and methyl (E)-2-{2-[6-(2-cyanophenoxy)pyrimidin-4-yloxy]phenyl}-3-methoxyacrylate (27%).

Characterising data for methyl 2-{2-[6-(2-cyanophenoxy)pyrimidin-4-yloxy]phenyl}-3,3-dimethoxypropanoate (the compound (I) where W is the methyl 2-(3,3-dimethoxy) propanoate group) which has the formula:

TABLE 2

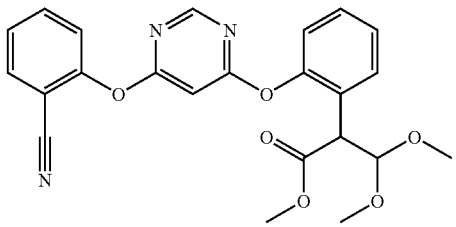

¹H NMR, 200 MHz in CDCl₃

| Chemical Shift (ppm) | Multiplicity | Integral | Coupling Constant (Hz) | Assignment |
|---|---|---|---|---|
| 8.32 | s | 1H | — | PyH2 |
| 7.66-7.55 | m | 3H | — | ArH |
| 7.31-7.09 | m | 5H | — | ArH |

TABLE 2-continued

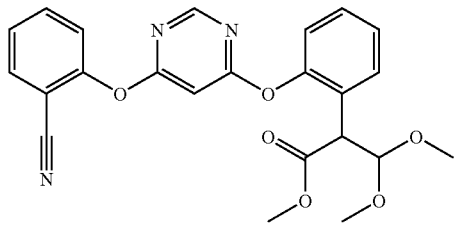

¹H NMR, 200 MHz in CDCl₃

| Chemical Shift (ppm) | Multiplicity | Integral | Coupling Constant (Hz) | Assignment |
|---|---|---|---|---|
| 6.44 | s | 1H | — | PyH5 |
| 4.95 | d | 1H | 9 | (CH₃O)₂CHCH |
| 4.18 | d | 1H | 9 | (CH₃O)₂CHCH |
| 3.50 | s | 3H | — | OCH₃ |
| 3.35 | s | 3H | — | OCH₃ |
| 3.11 | s | 3H | — | OCH₃ |

In the above table:
ArH are hydrogens bonded to phenyl rings;
Hydrogens shown in bold in the assignment column are those which relate to that particular signal;
'm' means multiplet signals; individual hydrogen signals are not fully resolved;
'd' means doublets;
's' means singlets;
Integrals indicates the number of hydrogens associated with the signal;
Pyrimidine hydrogens are denoted as PyHx where x refers to the position of attachment of the hydrogen to the pyrimidine ring.

Differential Scanning Calorimetry of some samples of methyl 2-{2-[6-(2-cyanophenoxy)pyrimidin-4-yloxy]phenyl}-3,3-dimethoxypropanoate show a melting endotherm at approximately 129° C., followed closely by an exothermic transition and another melting endotherm at approximately 139° C. This behaviour is strongly indicative of the existence of one (or more) polymorphic forms of this material, and the predominant polymorph is dependent on the crystallisation solvent and conditions. Powder x-ray diffraction before and after the 129° C. transition shows that different crystalline forms are present.

d) The preparation of azoxystrobin by the coupling of 2-cyanophenyl and methyl (E)-2-{2-[6-chloropyrimidin-4-yloxy]phenyl}-3-methoxyacrylate in MIBK/water with 1 mol % DABCO.

Methyl (E)-2-{2-[6-chloropyrimidin-4-yloxy]phenyl}-3-methoxyacrylate (20 g at 97.1% strength; prepared as described in WO 92/08703) was added to MIBK (77 ml) and water (11 ml), followed by 2-cyanophenyl (8.0 g), DABCO (0.07 g) and potassium carbonate (14.1 g). The reaction was heated to 80° C. and monitored for the end of the reaction (complete after 8 hours). The reaction mixture was washed with water at 80° C. Analysis of the MIBK layer revealed a 95.7% yield of methyl (E)-2-{2-[6-(2-cyanophenoxy)pyrimidin-4-yloxy]phenyl}-3-methoxyacrylate (azoxystrobin).

e) The preparation of azoxystrobin by the coupling of 2-cyanophenyl and methyl (E)-2-{2-[6-chloropyrimidin-4-yloxy]phenyl}-3-methoxyacrylate in MIBK with 1.5 mol % DABCO.

Methyl (E)-2-{2-[6-chloropyrimidin-4-yloxy]phenyl}-3-methoxyacrylate (98.4 g at 97.7% strength; prepared as described in WO 92/08703) was added to MIBK (214 g), and heated to 45-50° C. 2-cyanophenyl (40.1 g), potassium carbonate (63.4 g) and DABCO (0.51 g) were added and the temperature was raised to 80° C. and held at this temperature for 4.5 hours. Water (316 g) was added and agitation continued for 30 minutes before settling and separating the aqueous layer. Analysis of the MIBK solution revealed a 97.2% yield of methyl (E)-2-{2-[6-(2-cyanophenoxy)pyrimidin-4-yloxy]phenyl}-3-methoxyacrylate (azoxystrobin).

f) The preparation of azoxystrobin by the coupling of 2-cyanophenyl and methyl (E)-2-{2-[6-chloropyrimidin-4-yloxy]phenyl}-3-methoxyacrylate in MIBK/water with 1.5 mol % DABCO.

Methyl (E)-2-{2-[6-chloropyrimidin-4-yloxy]phenyl}-3-methoxyacrylate (98.4 g at 97.7% strength; prepared as described in WO 92/08703) was added to MIBK (210 g) and water (38.3 g) and heated to 45-50° C. 2-Cyanophenol (40.1 g), potassium carbonate (63.4 g) and DABCO (0.51 g) were added and the temperature was raised to 80° C. and held for 5.5 hours. Water (316 g) was added and agitation continued for 30 minutes before settling and separating the aqueous layer. Analysis of the MIBK solution revealed a 91.8% yield of methyl (E)-2-{2-[6-(2-cyanophenoxy)pyrimidin-4-yloxy]phenyl}-3-methoxyacrylate (azoxystrobin).

g) Coupling of methyl 2-[2-(6-chloropyrimidin-4-yloxy)phenyl]-3,3-dimethoxypropanoate with 2-cyanophenyl in isopropyl acetate with 1.3 mol % of DABCO To isopropyl acetate (80 g) was added in sequence, 2-cyanophenyl (15.02 g at 99%, 0.125 mols), potassium carbonate (23.39 g, 0.169 mols), methyl 2-[2-(6-chloropyrimidin-4-yloxy)phenyl]-3,3-dimethoxypropanoate (40.61 g at 98.3%, 0.113 mols), which contained methyl (E)-2-{2-[6-chloropyrimidin-4-yloxy]phenyl}-3-methoxyacrylate (0.69 g, 0.0022 mols) and finally DABCO (0.172 g, 0.0015 mols). A further charge of isopropyl acetate (80.3 g) was added and the mixture heated to reflux for 6.5 hours. The reaction was cooled to room temperature and after standing overnight was further cooled to 5° C., held for one hour and then filtered. The filter cake was slurry washed with water (2×100 g) and then dried under vacuum (45° C., 400 mbar). The dried solid contained methyl 2-[2-[6-(2-cyanophenoxy)-pyrimidin-4-yloxy]phenyl]-3,3-dimethoxy propanoate (90.8% w/w), 74.1% of theory and methyl (E)-2-{2-[6-(2-cyanophenoxy)pyrimidin-4-yloxy]phenyl}-3-methoxyacrylate (2.41% w/w), 2.1% of theory. The isopropyl acetate filtrates contained methyl 2-[2-[6-(2-cyanophenoxy)-pyrimidin-4-yloxy]phenyl]-3,3-dimethoxy propanoate (3.44% w/w), 8.75% of theory and methyl (E)-2-{2-[6-(2-cyanophenoxy)pyrimidin-4-yloxy]phenyl}-3-methoxyacrylate (1.8% w/w), 4.95% of theory. The combined yield of compound (I) where W is the methyl (E)-2-(3-methoxy)acrylate group $C(CO_2CH_3)=CHOCH_3$ or the methyl 2-(3,3-dimethoxy)propanoate group $C(CO_2CH_3)CH(OCH_3)_2$ was 89.8% of theory.

h) Coupling of methyl 2-[2-(6-chloropyrimidin-4-yloxy)phenyl]-3,3-dimethoxypropanoate with 2-cyanophenyl in cyclohexanone with 1.3 mol % DABCO To cyclohexanone (75.6 g) was added in sequence, 2-cyanophenyl (15.02 g at 99%, 0.125 mols), potassium carbonate (23.39 g, 0.169 mols), methyl 2-[2-(6-chloropyrimidin-4-yloxy)phenyl]-3,3-dimethoxypropanoate (40.61 g at 98.3%, 0.113 mols), which contained methyl (E)-2-{2-[6-chloropyrimidin-4-yloxy]phenyl}-3-methoxyacrylate (0.69 g, 0.0022 mols) and finally DABCO (0.172 g, 0.0015 mols). A further charge of cyclohexanone (76.3 g) was added and the mixture heated to 90° C. for 140 minutes. The cyclohexanone was removed by vacuum distillation. Water (100 g) and dichloromethane (200 g) were added to the distillation residues and the resulting mixture heated to 60° C. and held for 30 minutes. The mixture was filtered and the phases separated. The dichloromethane was distilled from the organic phase to yield a brown oily solid which was triturated with methanol (20 ml) to give a light beige solid. Some of the methanol was removed in vacuo and water (125 g) added. The resulting slurry was filtered, sucked dry on the filter and then dried in vacuo (45° C., 400 mbar). The dried solid contained methyl 2-[2-[6-(2-cyanophenoxy)-pyrimidin-4-yloxy]phenyl]-3,3-dimethoxy propanoate (81.19% w/w), 74.0% of theory and methyl (E)-2-{2-[6-(2-cyanophenoxy)pyrimidin-4-yloxy]phenyl}-3-methoxyacrylate (18.55% w/w), 18.3% of theory. The combined yield of compound (I) where W is the methyl (E)-2-(3-methoxy)acrylate group $C(CO_2CH_3)=CHOCH_3$ or the methyl 2-(3,3-dimethoxy)propanoate group $C(CO_2CH_3)CH(OCH_3)_2$ was 92.3% of theory.

i) Coupling of methyl (E)-2-{2-[6-chloropyrimidin-4-yloxy]phenyl}-3-methoxyacrylate with 2-cyanophenyl in N,N-diisopropylethylamine (Hunigs Base) with 1.0 mol % DABCO and using 1,8-diazabicyclo[5.4.0]undec-7-ene (DBU) as the base.

A slurry containing methyl (E)-2-{2-[6-chloropyrimidin-4-yloxy]phenyl}-3-methoxyacrylate (65.4 g at 98%, 0.2 mols), 2-cyanophenyl (26.8 g at 97.5%, 0.22 mols) and 1,8-diazabicyclo[5.4.0]undec-7-ene (DBU) (36.9 g at 99%, 0.24 mols) in N,N-diisopropylethylamine (105 mls) was heated to 50-60° C. A solution of DABCO (0.224 g, 0.002 mols) in N,N-diisopropylethylamine (10 mls) was added. The mixture was stirred at this temperature until the reaction was complete (3 hours). The solvent was removed by vacuum distillation to 90° C. Toluene (130 ml) was added to the distillation residues, maintaining the temperature between 70-80° C., followed by water (210 mls), maintaining the temperature as before. The mixture was stirred for 10 minutes at 80° C. and then settled and the lower aqueous phase separated. The toluene solution (180.2 g) contained methyl (E)-2-{2-[6-(2-cyanophenoxy)pyrimidin-4-yloxy]phenyl}-3-methoxyacrylate (39.1% w/w) 87.4% of theory.

j) Coupling of methyl (E)-2-{2-[6-chloropyrimidin-4-yloxy]phenyl}-3-methoxyacrylate with 2-cyanophenyl in isopropyl acetate with 1.0 mol % DABCO.

A slurry containing methyl (E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenyl (33.6 g at 97.5%, 0.275 mols) in isopropyl acetate (130 mls) was heated to approximately 60° C. A solution of DABCO (0.28 g, 0.0025 mols) in isopropyl acetate (10 mls) was added. The mixture was heated to 80° C. and held at this temperature for 360 minutes. The isopropyl acetate was removed by vacuum distillation to a maximum temperature of 80° C. Toluene (160 ml) was added to the distillation residues, maintaining the temperature between 60-70° C., followed by water (265 mls) which had been heated to 60° C., again maintaining the temperature between 60-70° C. The mixture was stirred for 40 minutes at 80° C. and then settled and the lower aqueous phase separated. The toluene solution (229.8 g) contained methyl (E)-2-{2-[6-(2-cyanophenoxy)pyrimidin-4-yloxy]phenyl}-3-methoxyacrylate (41.2% w/w) 94.2% of theory.

k) Coupling of methyl 2-[2-(6-chloropyrimidin-4-yloxy)phenyl]-3,3-dimethoxypropanoate with 2-cyanophenyl in isopropyl acetate with 1.3 mol % of DABCO To isopropyl acetate (160.3 g) at room temperature, was added, in sequence, 2-cyanophenyl (15.02 g at 99%, 0.125 mol), potassium carbonate (18.3 g, 0.13 mols) and methyl 2-[2-(6-chloropyrimidin-4-yloxy)phenyl]-3,3-dimethoxypropanoate (40.39 g at 98.84%, 0.113 mols), which contained methyl (E)-2-{2-[6-chloropyrimidin-4- yloxy]phenyl}-3-methoxyacrylate (0.29 g, 9.1×10$^{-4}$ mols). The mixture was heated to 60° C. and held for 10 minutes. DABCO (0.172 g, 0.0015 mols) was added and the mixture was heated to reflux (~90° C.). The reaction was complete in 6 hours. The mixture was cooled to 85° C. and water (100 g) added slowly such that the temperature did not go below 75° C. After stirring for 15 minutes the reaction was allowed to settle and the aqueous phase separated. A second water wash (100 g) was applied in the same manner. The washed organic phase (201.6 g) contained methyl 2-[2-[6-(2-cyanophenoxy)-pyrimidin-4-yloxy]phenyl]-3,3-dimethoxy propanoate (22.5% w/w), 91.45% of theory and methyl (E)-2-{2-[6-(2-cyanophenoxy)pyrimidin-4-yloxy]phenyl}-3-methoxyacrylate (1.00% w/w), 4.4% of theory. The combined yield of compound (I) where W is the methyl (E)-2-(3-methoxy)acrylate group C(CO$_2$CH$_3$)=CHOCH$_3$ or the methyl 2-(3,3-dimethoxy)propanoate group C(CO$_2$CH$_3$)CH(OCH$_3$)$_2$ was 95.85% of theory.

As can be seen, the conditions used in the processes described in Examples 2a) to k) give a good yield of azoxystrobin.

Example 3

This example concerns experiments carried out to investigate whether the order of addition of the components makes a difference to the yield of azoxystrobin obtained. In particular, this example investigates whether yields are greater if the DABCO is added as the last component.

a) Coupling of methyl (E)-2-{2-[6-chloropyrimidin-4-yloxy]phenyl}-3-methoxyacrylate with 2-cyanophenyl in MIBK with 1 mol % DABCO added after the 2-cyanophenyl, that is, last.

A slurry containing methyl (E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenyl (33.6 g at 97.5%, 0.275 mols) in MIBK (160 mls) was heated to approximately 60° C. A solution of DABCO (0.28 g, 0.0025 mols) in MIBK (10 mls) was added. The mixture was heated to 80° C. and held at this temperature for 360 minutes. Water (300 mls) was charged to the reaction, maintaining the temperature in the range 70-80° C. The mixture was stirred for 70 minutes then settled and the lower aqueous phase separated. The MIBK solution (235.3 g) contained methyl (E)-2-{2-[6-(2-cyanophenoxy)pyrimidin-4-yloxy]phenyl}-3-methoxyacrylate (41.0% w/w) 95.8% of theory.

b) Coupling of methyl (E)-2-{2-[6-chloropyrimidin-4-yloxy]phenyl}-3-methoxyacrylate with 2-cyanophenyl in MIBK with 1 mol % DABCO added before the 2-cyanophenyl.

To a slurry containing methyl (E)-2-{2-[6-chloropyrimidin-4-yloxy]phenyl}-3-methoxyacrylate (80.9 g at 99%, 0.25 mols) and potassium carbonate (52.8 g at 98%, 0.375 mols) in MIBK (160 mls) was added a solution of DABCO (0.28 g, 0.0025 mols) in MIBK (10 mls). The mixture was heated to around 60° C. and then 2-cyanophenyl (33.6 g at 97.5%, 0.275 mols) was charged. The mixture was heated to 80° C. and held at this temperature for 350 minutes. The reaction mixture was cooled to room temperature overnight and then reheated to 80° C. Water (300 mls) was charged to the reaction, maintaining the temperature in the range 70-80° C. The mixture was stirred for 40 minutes then settled and the lower aqueous phase separated. The MIBK solution (237.5 g) contained methyl (E)-2-{2-[6-(2-cyanophenoxy)pyrimidin-4-yloxy]phenyl}-3-methoxyacrylate (39.0% w/w) 91.9% of theory.

c) Coupling of methyl (E)-2-{2-[6-chloropyrimidin-4-yloxy]phenyl}-3-methoxyacrylate with 2-cyanophenyl in MIBK with 1 mol % DABCO added after the 2-cyanophenyl, that is, last.

A slurry containing methyl (E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenyl (33.6 g at 97.5%, 0.275 mols) in MIBK (160 mls) was heated to approximately 60° C. A solution of DABCO (0.28 g, 0.0025 mols) in MIBK (10 mls) was added. The mixture was heated to 80° C. and held at this temperature for 240 minutes (residual (E)-2-{2-[6-chloropyrimidin-4-yloxy]phenyl}-3-methoxyacrylate at the end of reaction was 4.4% by area on GC). Water (300 mls), at 60° C., was charged to the reaction, maintaining the temperature in the range 70-80° C. The mixture was stirred for 40 minutes then settled and the lower aqueous phase separated. The MIBK solution (237.1 g) contained methyl (E)-2-{2-[6-(2-cyanophenoxy)pyrimidin-4-yloxy]phenyl}-3-methoxyacrylate (38.7% w/w) 89.1% of theory.

d) Coupling of methyl (E)-2-{2-[6-chloropyrimidin-4-yloxy]phenyl}-3-methoxyacrylate with 2-cyanophenyl in MIBK with 1 mol % DABCO added before the 2-cyanophenyl.

To a slurry containing methyl (E)-2-{2-[6-chloropyrimidin-4-yloxy]phenyl}-3-methoxyacrylate (80.9 g at 99%, 0.25 mols) and potassium carbonate (52.8 g at 98%, 0.375 mols) in MIBK (160 mls) was added a solution of DABCO (0.28 g, 0.0025 mols) in MIBK (10 mls). The mixture was heated to around 60° C. and then 2-cyanophenyl (33.6 g at 97.5%, 0.275 mols) was charged. The mixture was heated to 80° C. and held at this temperature for 360 minutes (residual (E)-2-{2-[6-chloropyrimidin-4-yloxy]phenyl}-3-methoxyacrylate at the end of reaction was 5.8% by area on GC). Water (300 mls), at 60° C., was charged to the reaction, maintaining the temperature in the range 70-80° C. The mixture was stirred for 40 minutes then settled and the lower aqueous phase separated. The MIBK solution (232.6 g) contained methyl (E)-2-{2-[6-(2-cyanophenoxy)pyrimidin-4-yloxy]phenyl}-3-methoxyacrylate (35.3% w/w) 81.6% of theory.

In addition, in order to provide a comparison, Example 3e), below, gives an indication of the yield expected when higher concentrations of DABCO are used (2 mol %):

e) Coupling of methyl (E)-2-{2-[6-chloropyrimidin-4-yloxy]phenyl}-3-methoxyacrylate with 2-cyanophenyl in MIBK with 2 mol % DABCO.

To a slurry containing methyl (E)-2-{2-[6-chloropyrimidin-4-yloxy]phenyl}-3-methoxyacrylate (80.9 g at 99%, 0.25 mols) and potassium carbonate (52.8 g at 98%, 0.375 mols) in MIBK (160 mls) was added a solution of DABCO (0.56 g, 0.005 mols) in MIBK (10 mls). The mixture was heated to approximately 60° C. and then 2-cyanophenyl (33.6 g at 97.5%, 0.275 mols) was charged. The mixture was heated to 80° C. and held at this temperature for 280 minutes. Water (300 mls) was charged to the reaction, maintaining the temperature in the range 70-80° C. The mixture was stirred for 40 minutes then settled and the lower aqueous phase separated. The MIBK solution (237.0 g) contained methyl (E)-2-{2-[6-(2-cyanophenoxy)pyrimidin-4-yloxy]phenyl}-3-methoxyacrylate (40.2% w/w) 94.5% of theory.

A summary of the results of these experiments are shown in the following table:

TABLE 3

| Example | Concentration of DABCO | Solvent | DABCO added | Azoxystrobin recovered (% of theory) |
|---|---|---|---|---|
| 3a | 1.0 mol % | MIBK | Last | 95.8 |
| 3b | 1.0 mol % | MIBK | Before 2-cyanophenol | 91.9 |
| 3c | 1.0 mol % | MIBK | Last | 89.1[1] |
| 3d | 1.0 mol % | MIBK | Before 2-cyanophenol | 81.6[1] |
| 3e | 2.0 mol % | MIBK | Before 2-cyanophenol | 94.5 |

[1]Overall yield in these experiments is not indicative of the yield obtainable with 1.0 mol % DABCO in MIBK as the reactions did not reach completion.

As can be seen, surprisingly, the yield of azoxystrobin recovered from the process was increased when the DABCO was added after the 2-cyanophenyl.

It is noted that a comparison of Example 3e (2.0 mol % DABCO) with Examples 3a and 3b (1.0 mol % DABCO) confirms the results already obtained in Example 1 in a different solvent (DMF): the yields for experiments that had gone to completion with 1.0 mol % DABCO, surprisingly, are comparable to yields obtained using 2.0 mol % DABCO.

Example 4

This example concerns experiments carried out in an aqueous system.

a) Coupling of methyl 2-[2-(6-chloropyrimidin-4-yloxy)phenyl]-3,3-dimethoxypropanoate with 2-cyanophenyl in isopropyl acetate with 11.0 mol % of DABCO added after the potassium 2-cyanophenoxide solution, that is, last A stirred solution of methyl 2-[2-(6-chloropyrimidin-4-yloxy)phenyl]-3,3-dimethoxypropanoate (40.6 g at 99%, 0.113 mol) in isopropyl acetate (161.3 g) was heated to 50° C. and then an aqueous solution of potassium 2-cyanophenoxide (32.44 g at 46.0%, 0.126 mol) was added, followed by an aqueous solution of potassium carbonate (5.95 g at 40%, 0.017 mol) and an aqueous solution of DABCO (0.644 g at 20%, 0.00115 mol). The mixture was stirred under reflux for 5.5 hours, during which time the reflux temperature increased from 82° C. to 88° C. Water was removed in a Dean and Stark trap. The reaction mixture was washed with water (100 ml) at 70° C., followed by 1% aqueous HCl (100 ml) at 70° C. The isopropyl acetate solution (164.3 g) contained methyl 2-[2-[6-(2-cyanophenoxy)-pyrimidin-4-yloxy]phenyl]-3,3-dimethoxy propanoate (22.05% w/w), 75.4% of theory and methyl (E)-2-{2-[6-(2-cyanophenoxy)pyrimidin-4-yloxy]phenyl}-3-methoxyacrylate (3.04% w/w), 11% of theory. The combined yield of compound (I) where W is the methyl (E)-2-(3-methoxy)acrylate group C(CO$_2$CH$_3$)=CHOCH$_3$ or the methyl 2-(3,3-dimethoxy)propanoate group C(CO$_2$CH$_3$)CH(OCH$_3$)$_2$ was 86.4% of theory.

b) Coupling of methyl 2-[2-(6-chloropyrimidin-4-yloxy)phenyl]-3,3-dimethoxypropanoate with 2-cyanophenyl in isopropyl acetate with 1.4 mol % of DABCO added after the potassium 2-cyanophenoxide solution, that is, last A mixture of methyl 2-[2-(6-chloropyrimidin-4-yloxy)phenyl]-3,3-dimethoxypropanoate (96.0 g at 83.72%, 0.228 mols) which contained methyl (E)-2-{2-[6-chloropyrimidin-4-yloxy]phenyl}-3-methoxyacrylate (8.52 g, 0.0266 mols) and isopropyl acetate (305.4 g) was heated to 50° C. Potassium carbonate (27 g at 98%, 0.19 mols) and aqueous potassium 2-cyanophenoxide (90.0 g at 50%, 0.286 mols) were added, followed by an aqueous solution of DABCO (8.17 g at 5%, 0.0036 mols). The reaction mixture was heated at reflux for 225 minutes. Water was removed in a Dean and Stark Trap during the reaction. The mixture was cooled to 75° C. and water (241.4 g) added slowly. The mixture was stirred at 75° C. for 20 minutes, settled and the aqueous phase removed. A second charge of water (99.2 g) was added to the isopropyl acetate solution. The mixture was stirred at 75° C. for 30 minutes, settled and the aqueous phase removed. The organic phase (353.1 g) contained methyl 2-[2-[6-(2-cyanophenoxy)-pyrimidin-4-yloxy]phenyl]-3,3-dimethoxy propanoate (22.8% w/w) 72.6% of theory and methyl (E)-2-{2-[6-(2-cyanophenoxy)pyrimidin-4-yloxy]phenyl}-3-methoxyacrylate (4.47% w/w) 15.4% of theory. The combined yield of compound (I) where W is the methyl (E)-2-(3-methoxy)acrylate group C(CO$_2$CH$_3$)=CHOCH$_3$ or the methyl 2-(3,3-dimethoxy)propanoate group C(CO$_2$CH$_3$)CH(OCH$_3$)$_2$ was 88% of theory.

c) Coupling of methyl 2-[2-(6-chloropyrimidin-4-yloxy)phenyl]-3,3-dimethoxypropanoate with 2-cyanophenyl in isopropyl acetate with 1.4 mol % of DABCO added after the potassium 2-cyanophenoxide solution, that is last A mixture of methyl 2-[2-(6-chloropyrimidin-4-yloxy)phenyl]-3,3-dimethoxypropanoate (69.4 g at 83.72%, 0.165 mols), which contained methyl (E)-2-{2-[6-chloropyrimidin-4-yloxy]phenyl}-3-methoxyacrylate (6.16 g, 0.019 mols) and isopropyl acetate (220.8 g) was heated to 50° C. and stirred at this temperature for 10 minutes. Aqueous potassium carbonate (19.5 g at 40%, 0.0565 mols) followed by aqueous potassium 2-cyanophenoxide (65.0 g at 50%, 0.207 mols). Finally an aqueous solution of DABCO (5.91 g at 5.0%, 0.0026 mols) was added. The reaction mixture was heated at reflux for 300 minutes. Water was removed in a Dean and Stark Trap during the reaction. The mixture was cooled to 70-75° C. and water (174.5 g) added slowly to maintain the temperature. The mixture was stirred at 75° C. for 20 minutes, settled and the aqueous phase removed. A second charge of water (71.7 g) was added to the isopropyl acetate solution. The mixture was stirred at 75° C. for 20 minutes, settled and the aqueous phase removed. The organic phase (233.1 g) contained methyl 2-[2-[6-(2-cyanophenoxy)-pyrimidin-4-yloxy]phenyl]-3,3-dimethoxy propanoate (25.09% w/w), 73% of theory and methyl (E)-2-{2-[6-(2-cyanophenoxy)pyrimidin-4-yloxy]phenyl}-3-methoxyacrylate (4.96% w/w), 15.6% of theory. The combined yield of compound (I) where W is the methyl (E)-2-(3-methoxy)acrylate group C(CO$_2$CH$_3$)=CHOCH$_3$ or the methyl 2-(3,3-dimethoxy)propanoate group C(CO$_2$CH$_3$)CH(OCH$_3$)$_2$ was 88.6% of theory.

d) Coupling of methyl 2-[2-(6-chloropyrimidin-4-yloxy)phenyl]-3,3-dimethoxypropanoate with 2-cyanophenyl in isopropyl acetate with 1.4 mol % of DABCO added before the potassium 2-cyanophenoxide solution.

A mixture of methyl 2-[2-(6-chloropyrimidin-4-yloxy)phenyl]-3,3-dimethoxypropanoate (99.0 g at 83.72%, 0.235 mols), which contained methyl (E)-2-{2-[6-chloropyrimidin-4-yloxy]phenyl}-3-methoxyacrylate (8.78 g, 0.0274 mols) and isopropyl acetate (314.9 g) was heated to 50° C. and stirred at this temperature for 10 minutes. Aqueous potassium carbonate (27.8 g at 40%, 0.081 mols) followed by an aqueous solution of DABCO (8.42 g at 5%, 0.0038 mols) was added. Finally aqueous potassium 2-cyanophenoxide (92.8 g at 50%, 0.295 mols) was charged. The reaction mixture was heated at reflux for 260 minutes. Water was removed in a Dean and Stark Trap during the reaction. The mixture was cooled to 70° C. and water (249 g) added slowly. The mixture was stirred at 75° C. for 20 minutes, settled and the aqueous phase removed. A second charge of water (102.3 g) was added to the isopropyl acetate solution. The mixture was stirred at 75° C. for 20 minutes, settled and the aqueous phase removed. The organic phase (373.2 g) contained methyl 2-[2-[6-(2-cyanophenoxy)-pyrimidin-4-yloxy]phenyl]-3,3-dimethoxy propanoate (20.8% w/w) 68% of theory and methyl (E)-2-{2-[6-(2-cyanophenoxy)pyrimidin-4-yloxy]phenyl}-3-methoxyacrylate (3.52% w/w) 12.4% of theory. The combined yield of compound (I) where W is the methyl (E)-2-(3-methoxy)acrylate group $C(CO_2CH_3)=CHOCH_3$ or the methyl 2-(3,3-dimethoxy)propanoate group $C(CO_2CH_3)CH(OCH_3)_2$ was 80.4% of theory.

A summary of the results of these experiments is shown in the following table:

TABLE 4

| Example | Concentration of DABCO | Solvent | DABCO added | Azoxystrobin recovered (% of theory) |
|---|---|---|---|---|
| 4a | 1.0 mol % | isopropyl acetate | Last | 86.4 |
| 4b | 1.4 mol % | isopropyl acetate | Last | 88.0 |
| 4c | 1.4 mol % | isopropyl acetate | Last | 88.6 |
| 4d | 1.4 mol % | isopropyl acetate | Before 2-cyanophenol salt | 80.4 |

It can be seen from these results that the process of the present invention may also be carried out in an aqueous system. In addition, the surprising result seen in Example 3, with respect to the order of addition of DABCO, is also seen in the aqueous system—adding DABCO after the 2-cyanophenyl (in the form of potassium 2-cyanophenoxide), that is, last, provides a higher yield than adding it before.

Example 5

The preparation of methyl (E)-2-(2-hydroxyphenyl)-3-(methoxy)acrylate

Step 1: The preparation of methyl 2-[(2-benzyloxy)phenyl]-(3,3-dimethoxy)propanoate.

Crude methyl 2-(2-hydroxyphenyl)-3,3-(dimethoxy)propanoate (15 g), DMF (82 g) and potassium carbonate 8.7 g were agitated at room temperature and benzyl bromide (9.8 g) added over 15 minutes. After 6 hours a further charge of benzyl bromide (1.0 g) was added. After stirring overnight, water (200 ml) was added. The solid which formed was isolated by suction filtration, washed with water and sucked dry on the filter to give methyl 2-[(2-benzyloxy)phenyl]-(3,3-dimethoxy)propanoate (57%).

Step 2: The preparation of methyl (E)-2-(2-benzyloxy)phenyl-3-methoxyacrylate.

A solution of methyl 2-[(2-benzyloxy)phenyl]-(3,3-dimethoxy)propanoate (5 g; from Step 1) in acetic anhydride (7.0 g) was heated to 40° C. and methanesulphonic acid (0.33 g) added. After 90 minutes the mixture was allowed to cool to room temperature and toluene (25 ml) was added. The resulting solution was washed with water (3×75 ml) and then the toluene was evaporated in vacuo to give a liquid. After standing overnight crystals formed. These were isolated by filtration. A second crop was isolated from the filtrates after further concentration and trituration with ethanol.

The combined yield of methyl (E)-2-(2-benzyloxy)phenyl-3-methoxyacrylate was 44%.

Step 3: The preparation of methyl (E)-2-(2-hydroxy)phenyl-3-methoxyacrylate.

Ethyl acetate (25 ml) was degassed by application of vacuum and purged with nitrogen. Methyl (E)-2-(2-benzyloxy)phenyl-3-methoxyacrylate (0.8 g) and palladium on charcoal (0.02 g) was added in ethyl acetate (10 ml). The nitrogen atmosphere was replace by hydrogen and the reaction allowed to stir at ambient temperature. After approximately 40 hours the catalyst was filtered off and the reaction re-started with fresh catalyst (0.02 g). After 2 hours the reaction was complete. The reaction flask was purged with nitrogen. The catalyst was filtered, washed with ethyl acetate and the combined filtrates and washes evaporated under vacuum to give methyl (E)-2-(2-hydroxy)phenyl-3-methoxyacrylate as an oil, which crystallised on standing.

Characterising data (see Table 5) for methyl 2-(2-benzyloxy)phenyl-3,3-dimethoxypropanoate (the compound (V) where Q is benzyl) which has the formula:

TABLE 5

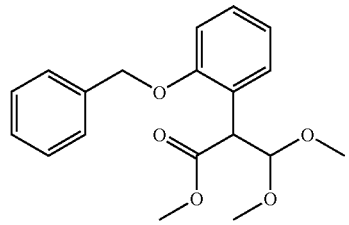

$^1$H NMR, 200 MHz in CDCl$_3$

| Chemical Shift (ppm) | Multiplicity | Integral | Coupling Constant (Hz) | Assignment |
|---|---|---|---|---|
| 7.44-7.13 | m | 7H | — | ArH |
| 6.93-6.85 | m | 2H | — | ArH |
| 5.04 | s | 2H | — | ArCH$_2$O |
| 5.0 | d | 1H | 9 | (CH$_3$O)$_2$CHCH |
| 4.56 | d | 1H | 9 | (CH$_3$O)$_2$CHCH |
| 3.58 | s | 3H | — | OCH$_3$ |
| 3.38 | s | 3H | — | OCH$_3$ |
| 3.10 | s | 3H | — | OCH$_3$ |

Characterising data (see Table 6) for methyl (E)-2-(2-benzyloxy)phenyl-3-methoxyacrylate which has the formula:

TABLE 6

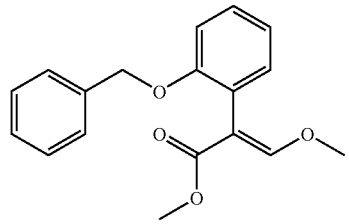

$^1$H NMR, 200 MHz in CDCl$_3$

| Chemical Shift (ppm) | Multiplicity | Integral | Coupling Constant (Hz) | Assignment |
|---|---|---|---|---|
| 7.43 | s | 1H | — | CH3OCH= |
| 7.3-6.85 | m | ~9H | — | ArH |
| 4.99 | s | 2H | — | ArCH$_2$O |
| 3.71 | s | 3H | — | OCH$_3$ |
| 3.57 | s | 3H | — | OCH$_3$ |

Characterising data (see Table 7) for methyl (E)-2-(2-hydroxy)phenyl-3-methoxyacrylate (the compound (IV) where W is the methyl (E)-2-(3-methoxy)acrylate group) which has the formula:

TABLE 7

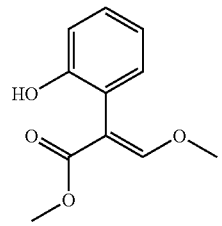

| Chemical Shift (ppm) | Multiplicity | Integral | Coupling Constant (Hz) | Assignment |
|---|---|---|---|---|
| 7.56 | s | 1H | — | CH3OCH= |
| 7.2-7.06 | m | ~2H | — | ArH |
| 6.9-6.8 | m | 2H | — | ArH |
| 3.80 | s | 3H | — | $OCH_3$ |
| 3.69 | s | 3H | — | $OCH_3$ |

$^1$H NMR, 200 MHz in $CDCl_3$

In the above tables:
ArH are hydrogens bonded to phenyl rings,
Hydrogens shown in bold in the assignment column are those which relate to that particular signal,
'm' means multiplet signals; individual hydrogen signals are not fully resolved,
'd' means doublets,
's' means singlets,
Integrals indicates the number of hydrogens associated with the signal.

The invention claimed is:

1. A process for preparing a compound of formula (I):

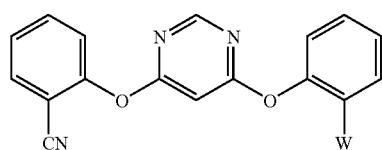

(I)

which comprises either
(a) reacting a compound of formula (II):

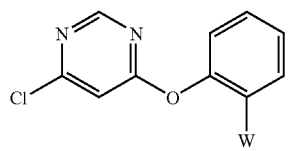

(II)

with 2-cyanophenol, or a salt thereof, in the presence of between 0.1 and 2 mol % of 1,4-diazabicyclo[2.2.2]octane, or (b) reacting a compound of the formula (III):

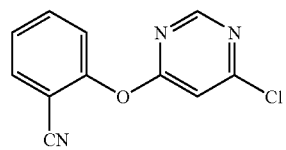

(III)

with a compound of the formula (IV):

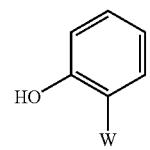

(IV)

in the presence of between 0.1 and 2 mol % of 1,4-diazabicyclo[2.2.2]octane;
where W is the methyl (E)-2-(3-methoxy)acrylate group $C(CO_2CH_3)$=$CHOCH_3$ or the methyl 2-(3,3-dimethoxy)propanoate group $C(CO_2CH_3)CH(OCH_3)_2$, or a mixture of the two groups.

2. The process according to claim 1 which is carried out in the presence of between 0.2 and 1.4 mol % of 1,4-diazabicyclo[2.2.2]octane.

3. The process according to claim 1 which is carried out in an inert solvent or diluent.

4. The process according to claim 3 in which the inert solvent or diluent is methyl isobutyl ketone, cyclohexanone, N,N-diisopropylethylamine, isopropyl acetate or N,N-dimethylformamide.

5. The process according to claim 4 in which the inert solvent or diluent is N,N-dimethylformamide.

6. The process according to claim 1 which is carried out in the presence of 1.0 mol % of 1,4-diazabicyclo[2.2.2]octane.

7. The process according to claim 1 which is carried out in an aqueous system.

8. The process according to claim 7 wherein, as a salt of 2-cyanophenol, potassium 2-cyanophenoxide is used.

9. The process according to claim 1 which is carried out in the presence of an acid acceptor.

10. The process according to claim 9 in which the acid acceptor is potassium carbonate or sodium carbonate.

11. The process according to claim 1 which is carried out at a temperature of from 0 to 100° C.

12. The process according to claim 1 in which the 1,4-diazabicyclo-[2.2.2]octane is the last component added.

* * * * *